(12) United States Patent
Kim et al.

(10) Patent No.: US 7,599,738 B2
(45) Date of Patent: Oct. 6, 2009

(54) SYNCHRONIZED VENTRICULAR PACING TO PROMOTE ATRIAL SENSING

(75) Inventors: Jaeho Kim, Redmond, WA (US); Joseph M. Bocek, Seattle, WA (US); Anthony S. Harrington, Woodinville, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 311 days.

(21) Appl. No.: 11/130,671

(22) Filed: May 17, 2005

(65) Prior Publication Data

US 2006/0265016 A1 Nov. 23, 2006

(51) Int. Cl.
*A61N 1/362* (2006.01)
(52) U.S. Cl. .......................................................... 607/9
(58) Field of Classification Search ................ 607/9
See application file for complete search history.

(56) References Cited

U.S. PATENT DOCUMENTS

| 5,601,613 A | 2/1997 | Florio et al. |
| 5,788,717 A | 8/1998 | Mann et al. |
| 5,792,192 A | 8/1998 | Lu |
| 5,814,083 A | 9/1998 | Hess et al. |
| 6,128,533 A * | 10/2000 | Florio et al. ............ 607/9 |
| 6,889,079 B2 * | 5/2005 | Bocek et al. ............ 607/9 |
| 6,957,104 B2 * | 10/2005 | Wagner ................... 607/9 |

* cited by examiner

*Primary Examiner*—George R Evanisko
*Assistant Examiner*—Amanda Patton
(74) *Attorney, Agent, or Firm*—Hollingsworth & Funk

(57) ABSTRACT

Methods and systems are described that involve synchronized ventricular pacing that promotes sensing of atrial events. The atrioventricular pacing delay is modified based on characteristics of previously sensed atrial events. The modified AV delay is implemented relative to a first atrial event. A second AV delay is implemented relative to a second atrial event if the second atrial event is sensed during the modified AV delay. A ventricular pacing pulse is delivered following the second AV delay.

17 Claims, 7 Drawing Sheets

SYNCHRONIZED VENTRICULAR PACING TO PROMOTE ATRIAL SENSING

FIELD OF THE INVENTION

The present invention relates generally to implantable medical devices and, more particularly, to detecting atrial tachycardia.

BACKGROUND OF THE INVENTION

Proper cardiac function relies on the synchronized contractions of the heart at regular intervals. When normal cardiac rhythm is initiated at the sinoatrial node, the heart is said to be in sinus rhythm. However, due to electrophysiologic disturbances caused by a disease process or from an electrical disturbance, the heart may experience irregularities in its coordinated contraction. In this situation, the heart is denoted to be arrhythmic. The resulting cardiac arrhythmia impairs cardiac efficiency and can be a potential life threatening event.

Cardiac arrhythmias occurring in the atria of the heart, for example, are called supra-ventricular tachyarrhythmias (SVTs). SVTs take many forms, including atrial fibrillation and atrial flutter. Both conditions are characterized by rapid, contractions of the atria. Cardiac arrhythmias occurring in the ventricular region of the heart, by way of further example, are called ventricular tachyarrhythmias. Ventricular tachyarrhythmias (VTs), are conditions denoted by a rapid heart beat, 150 to 250 beats per minute, originating from a location within the ventricular myocardium. Ventricular tachyarrhythmia can quickly degenerate into ventricular fibrillation (VF). Ventricular fibrillation is a condition denoted by extremely rapid, non synchronous contractions of the ventricles. This condition is fatal unless the heart is returned to sinus rhythm within a few minutes.

Implantable cardioverter/defibrillators (ICDs) have been used as an effective treatment for patients with serious tachyarrhythmias. ICDs are able to recognize and treat tachyarrhythmias with a variety of tiered therapies. These tiered therapies range from providing anti-tachycardia pacing pulses or cardioversion energy for treating tachyarrhythmias to high energy shocks for treating atrial and/or ventricular fibrillation. To effectively deliver these treatments, the ICD must first detect that a tachyarrhythmia that is occurring, after which appropriate therapy may be provided to the heart.

For the reasons stated above, and for other reasons stated below which will become apparent to those skilled in the art upon reading the present specification, there is a need in the art for reliably and accurately recognize types of cardiac rhythms produced by the heart. The present invention fulfills these and other needs.

SUMMARY OF THE INVENTION

The present invention is directed to a systems and methods for detecting atrial tachyarrhythmia. One embodiment of the invention involves a method for cardiac pacing that promotes atrial sensing. The method includes providing a first atrioventricular (AV) delay used for pacing a ventricle. The first atrioventricular (AV) delay is modified based on characteristics of previously sensed atrial events. The modified AV delay is implemented relative to a first atrial event. A second AV delay is implemented relative to a second atrial event if the second atrial event is sensed during the modified AV delay. A ventricular pacing pulse is delivered relative to the second AV delay.

The first atrial event may comprise, for example, a non-refractory event. The first AV delay may be modified according to various implementations. In one example, the first AV delay may be modified by extending the first AV delay if the atrial rate exceeds a maximum tracking rate. In another example, the first AV may be modified based on detection of premature atrial contraction. In yet another example, the first atrioventricular delay may be modified based on detection of a short-long pattern of atrial events.

According to aspects of the invention, the duration of the second AV delay is selected to enhance sensing of subsequent atrial events and may be based on a post ventricular atrial blanking (PVAB) interval.

Another embodiment of the invention involves a method of cardiac pacing during atrial flutter. Cardiac pacing is delivered using an atrioventricular delay interval. Atrial flutter is detected and a pacing response to the atrial flutter is implemented. The pacing response includes initiating one or more timing intervals based on detection of an atrial event sensed during a post ventricular atrial refractory period. An alternate atrioventricular delay is implemented during at least one of the timing intervals. A ventricular pacing pulse is delivered relative to the alternate atrioventricular interval. The alternate atrioventricular delay may be implemented to place an atrial refractory period between atrial events and/or to promote sensing of atrial events, for example.

Yet another embodiment of the invention is directed to a cardiac pacing device. The pacing device includes sensing circuitry configured to sense electrical signals of an atrium. A pulse generator is configured to deliver electrical stimulation to a ventricle. A processor is coupled to the sensing circuitry and the pulse generator. The processor is configured to provide a first atrioventricular delay used for pacing and to modify the first atrioventricular delay based on characteristics of one or more previous atrial events. The processor is configured to implement the modified AV delay and to implement a second AV delay relative to a second atrial event if the second atrial event is sensed during the modified AV delay. The processor controls delivery of a ventricular pacing pulse relative to the second AV delay.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 2-3 are timing diagrams illustrating undersensing of atrial events;

Figure 1A:
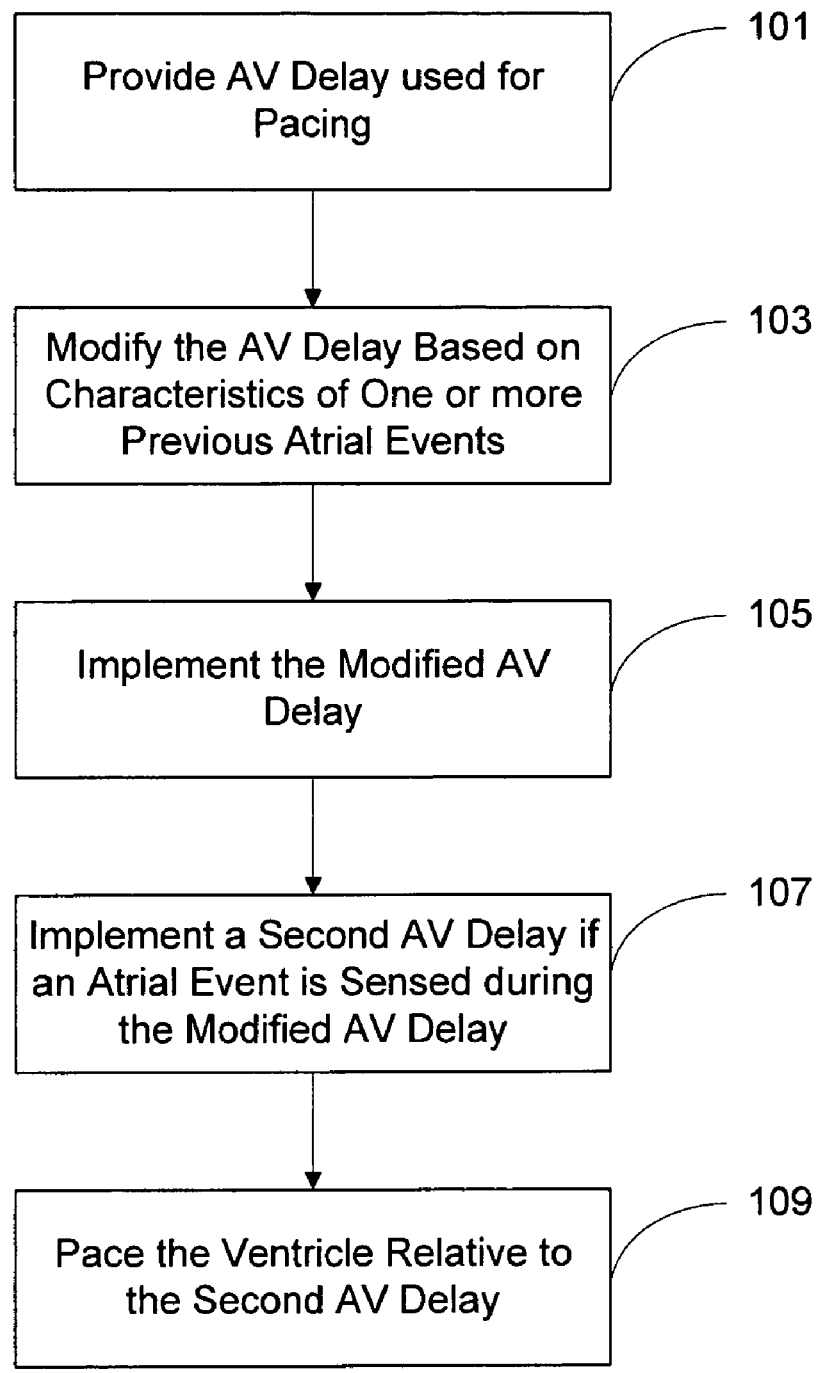
FIGS. 1A and 1B are flowcharts illustrating methods of synchronized ventricular pacing to promote atrial sensing in accordance with embodiments of the invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

A cardiac rhythm management (CRM) device, such as an implantable cardiac pacemaker/defibrillator (PD), typically includes circuitry for sensing cardiac signals and for delivering electrical stimulation to one or more heart chambers. Such a device may be programmed to recognize various cardiac rhythms and provide treatment to convert, interrupt, or mitigate dangerous rhythms. A tiered approach to therapy may be implemented, wherein some rhythms are treated with a less aggressive therapy, such as anti-tachycardia pacing (ATP), other rhythms are treated with a more aggressive therapy, such as high energy cardioversion or defibrillation shocks, and some arrhythmias are left untreated.

In addition to providing the therapies described above, the CRM may also respond to tachyarrhythmias by altering pacing delivered to the patient. For example, in atrial tracking modes, a fast atrial rhythm may cause the CRM device to pace the ventricle at an inappropriately high rate. Typically, pacemakers are programmed with a maximum tracking rate (MTR) that prevents the pacemaker from delivering ventricular pacing at a rate exceeding the MTR.

If the atrial rate increases beyond the MTR, some atrial events may occur during the post ventricular atrial refractory periods (PVARPs), causing the sensed atrial rate to drop so that a ventricular pulse is triggered by every other atrial event. This upper rate pacing behavior is sometimes referred to as 2:1 block.

The CRM device may respond to a detected atrial tachyarrhythmia by switching the pacing mode from an atrial tracking mode, such as DDD(R) or VDD(R) to a non-atrial tracking mode, such as DDI(R) or VDI(R). In one implementation, if the atrial rate exceeds a trigger rate, denoted the atrial tachyarrhythmia response (ATR) rate, then the mode switch occurs. Mode switching limits the amount of time ventricular pacing occurs at the maximum tracking rate or exhibits N:1 pacing behavior. When the atrial tachyarrhythmia episode terminates, the pacing mode may be switched back to the atrial tracking mode.

Discriminating between different types of atrial tachyarrhythmia allows the CRM device to select an appropriate therapy tailored for the particular type of tachyarrhythmia. For example, some atrial tachyarrhythmias are responsive to pacing therapy whereas others are more effectively treated with shock therapy. The ability to determine the type of atrial tachyarrhthmia before delivering therapy may reduce the number of shocks delivered to the patient, thus increasing the comfort of the patient and extending the device lifetime.

Detecting atrial tachyarrhythmia may involve, for example, determining if the atrial rate exceeds a threshold value. In one implementation, two or more programmable rate zones may be used for atrial tachyarrhythmia detection. If the atrial rate falls into a first rate zone, it is classified as a first type of atrial arrhythmia and a first therapy may be delivered. If the atrial rate falls into a second rate zone, the atrial arrhythmia is classified as a second type of atrial arrhythmia and a second therapy may be delivered.

In an alternate implementation, a rate threshold may be used to detect a fast atrial rate. The atrial rhythm may be further evaluated based on stability, morphology, pattern, and/or other characteristics to determine the particular type of atrial arrhythmia.

Accurate detection of atrial tachyarrhythmia involves accurate sensing of the intrinsic atrial events of an arrhythmic episode. Sensing atrial events occurring at a high rate is complicated due to atrial blanking periods that are implemented by the device following ventricular sensed or paced events. If atrial events fall within the blanking periods, they may not be sensed or counted toward detection of atrial tachyarrhythmia. These unsensed atrial events cause errors in atrial tachyarrhythmia detection, in classifying the type of atrial tachyarrhythmia, and in triggering pace mode switching. Undersensing of atrial events may be more pronounced during bi-ventricular pacing which involves additional or extended blanking periods during the cardiac cycle.

Undersensing of atrial events may be reduced or avoided if the atrial refractory period including the post ventricular atrial blanking period (PVAB) occurs between atrial events. Embodiments of the invention are directed to methods and systems for synchronizing ventricular pacing with atrial events to increase the likelihood of the atrial refractory period occurring between atrial events.

FIG. 1A is flowchart illustrating a method of synchronized ventricular pacing to promote atrial sensing in accordance with embodiments of the invention. A first atrioventricular (AV) delay is provided 101 for ventricular pacing. The first AV delay is modified 103 based on characteristics of one or more previously sensed atrial events. For example, the AV delay may be modified based the rate or pattern of previously sensed atrial events. The modified AV delay is implemented 105 relative to a first atrial event. A second AV delay is implemented 107 if a second atrial event is sensed during the modified AV delay. The ventricle is paced 109 relative to the second AV delay. Pacing the ventricle based on the second atrial event places the next atrial refractory period within atrial events, thus enhancing atrial sensing.

Figure 1B:
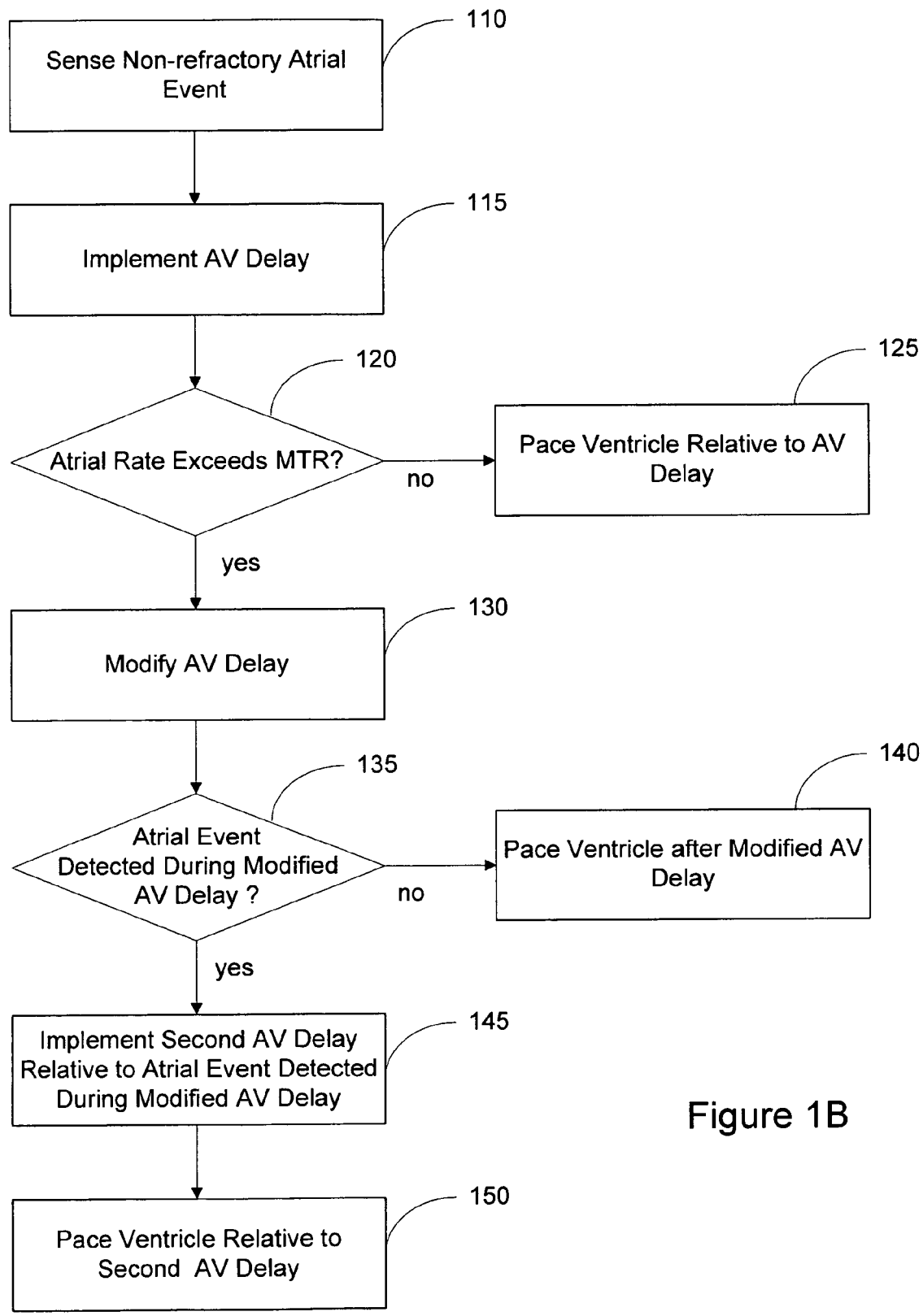

FIG. 1B is a flowchart illustrating a method of synchronized ventricular pacing in accordance with another embodiment of the invention. A non-refractory atrial event is sensed 110 and an atrioventricular (AV) pacing delay is implemented 115 relative to the atrial event. If the atrial beats are occurring 120 at a rate below the maximum tracking rate (MTR), then the ventricle is paced 125 after expiration of the AV delay. If the atrial beats are occurring 120 at a rate above the MTR, then the AV delay is modified 130. In one implementation, the AV delay may be extended to an interval indicative of atrial tachyarrhythmia, e.g., an atrial tachyarrhythmia detection interval.

If an atrial event is sensed 135 during the modified AV delay, then a second AV delay is implemented 145 relative to the sensed atrial event. The ventricle is paced 150 following the second AV delay. The second AV delay is typically shorter than the first, for example, the second AV delay may comprise an interval of about 10 ms. The second AV delay may be selected to maintain adequate pumping action of the heart and to promote atrial sensing. If an atrial event is not sensed 135 during the modified AV delay, the ventricle is paced 140 following the modified AV delay.

Figure 2:
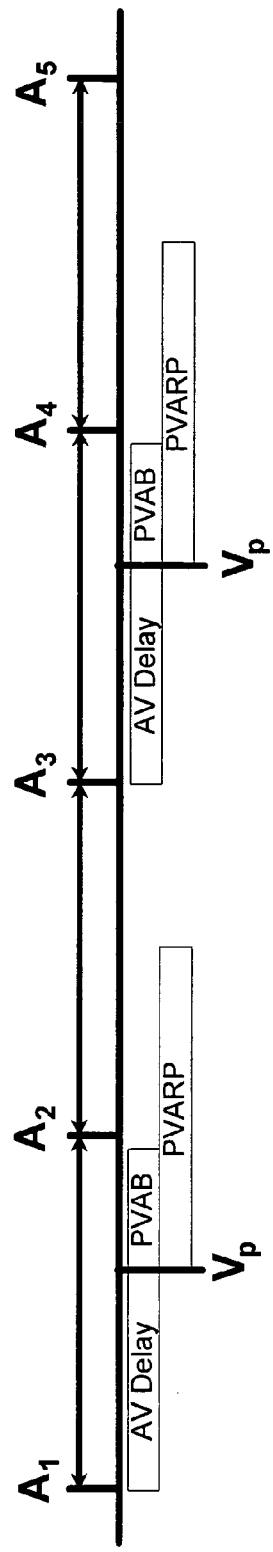
FIGS. 2-4 are timing diagrams illustrating
Figure 3:
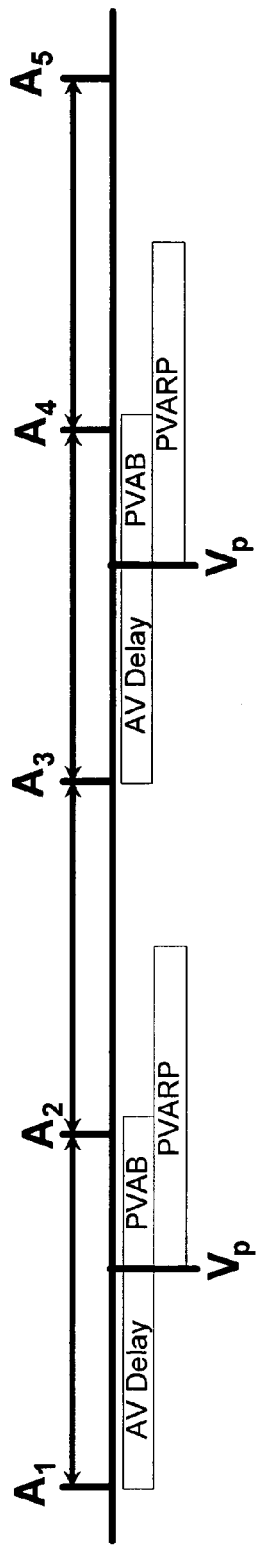
Figure 4:
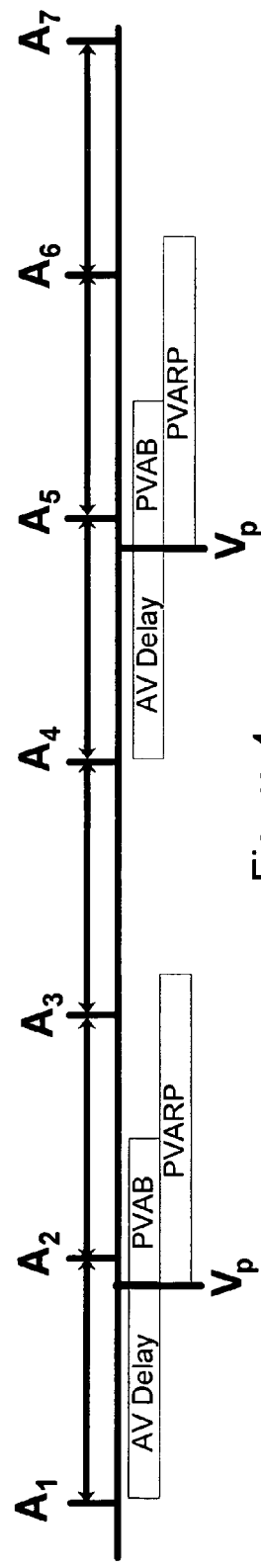

FIG. 2-4 are timing diagrams illustrating undersensing of atrial events. The timing diagram of FIG. 2 illustrates atrial flutter (AFL) resulting in 2:1 ventricular pacing with no undersensing of atrial events. Following the first atrial event, A1, a pacing cycle is initiated. An AV delay is initiated and the ventricle is paced, Vp, at the end of the AV delay. Following the ventricular pacing pulse, a cross chamber blanking period, PVAB, and a cross chamber refractory period, PVARP, are initiated. A second atrial event, A2, occurs during the PVARP, but after expiration of the PVAB. Thus, A2 is sensed, but is not used to initiate a pacing cycle.

The next pacing cycle is initiated by the third atrial event, A3, and is similar to the pacing cycle initiated by A1. A ventricular pacing pulse occurs after expiration of the AV delay. Cross chamber blanking and refractory periods, PVAB and PVARP, follow the ventricular pace. The next atrial event, A4, is sensed following expiration of PVAB but before expiration of PVARP. Because A4 is sensed during PVARP, A4 is not used to initiate a new pacing cycle. The pacing illustrated in FIG. 2 is representative of 2:1 pacing behavior, wherein every other atrial event causes a pacing cycle to be initiated and the ventricle is paced at approximately one-half the atrial rate.

FIG. 3 is a timing diagram illustrating AFL producing 2:1 ventricular pacing with undersensing of atrial events. As illustrated in FIG. 3, every other atrial event is unsensed and every other atrial event initiates a pacing cycle. Following the first atrial event, A1, a pacing cycle is initiated. The ventricle is paced, Vp, at the end of the AV delay. Following Vp, a cross chamber blanking period, PVAB, and a cross chamber refractory period, PVARP, are initiated. A second atrial event, A2, occurs during PVAB. Thus, A2 is not sensed and is not used to initiate the next pacing cycle.

The third pacing cycle is initiated by the third atrial event, A3, and is similar to the pacing cycle initiated by A1. A Vp occurs after expiration of the AV delay. Cross chamber blanking and refractory periods, PVAB and PVARP, follow the ventricular pace. The next atrial event, A4, is sensed during PVAB and is not sensed.

FIG. 4 illustrates AFL with 3:1 ventricular pacing and atrial undersensing. In this situation, every other atrial event is sensed and one out of three atrial events initiates a pacing cycle. Following the first atrial event, A1, a pacing cycle is initiated. A pacing pulse, Vp, is delivered at the end of the AV delay. Following Vp, a cross chamber blanking period, PVAB, and a cross chamber refractory period, PVARP, are initiated. A second atrial event, A2, occurs during PVAB. Thus, A2 is not sensed and is not used to initiate the next pacing cycle. The next atrial event A3 is sensed during PVARP of the first pacing cycle. A3 is sensed, but is not used to start a pacing cycle.

The next pacing cycle is initiated by the fourth atrial event, A4, and is similar to the pacing cycle initiated by A1. A Vp is delivered after expiration of the AV delay. Cross chamber blanking and refractory periods, PVAB and PVARP, follow the ventricular pace. A5 is sensed during PVAB and is not sensed nor used to start a pacing cycle. A6 is sensed during PVARP and is sensed, but is not used to start a pacing cycle.

Atrial tachyarrhythmia may be detected by counting the number of A-A intervals that fall into one or more atrial tachyarrhythmia rate zones. Undersensing of atrial events, as illustrated in the examples of FIGS. 3 and 4, may cause failure or delays in satisfying rate zone detection counters used in detection of atrial tachyarrhythmia. Further, the long A-A intervals caused by atrial undersensing may cause errors in the classification of types of atrial tachyarrhythmia, e.g., atrial fibrillation vs. atrial flutter. Further, undersensed atrial events may cause delays in implementation of atrial tachyarrhythmia therapy or inappropriate mode switching. For example, atrial undersensing may cause delays in mode switching or oscillations in switching back and forth between tracking mode and non-tracking mode. As described below in accordance with various exemplary embodiments, the problems associated with atrial undersensing may be reduced by using ventricular pacing synchronized to atrial events in accordance with embodiments of the invention.

Figure 5A:
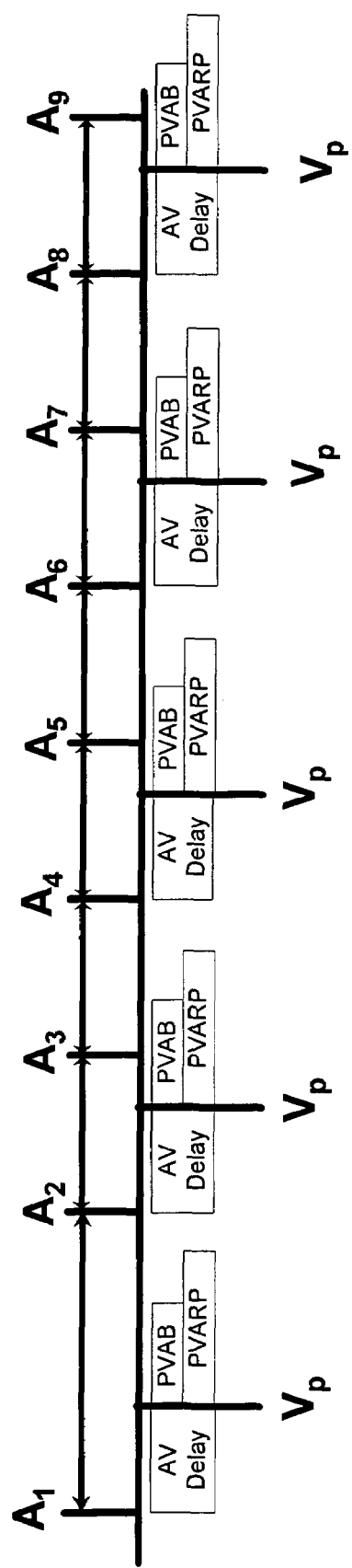
FIGS. 5A and 5B are timing diagrams illustrating synchronized ventricular pacing in accordance with embodiments of the invention.
Figure 5B:
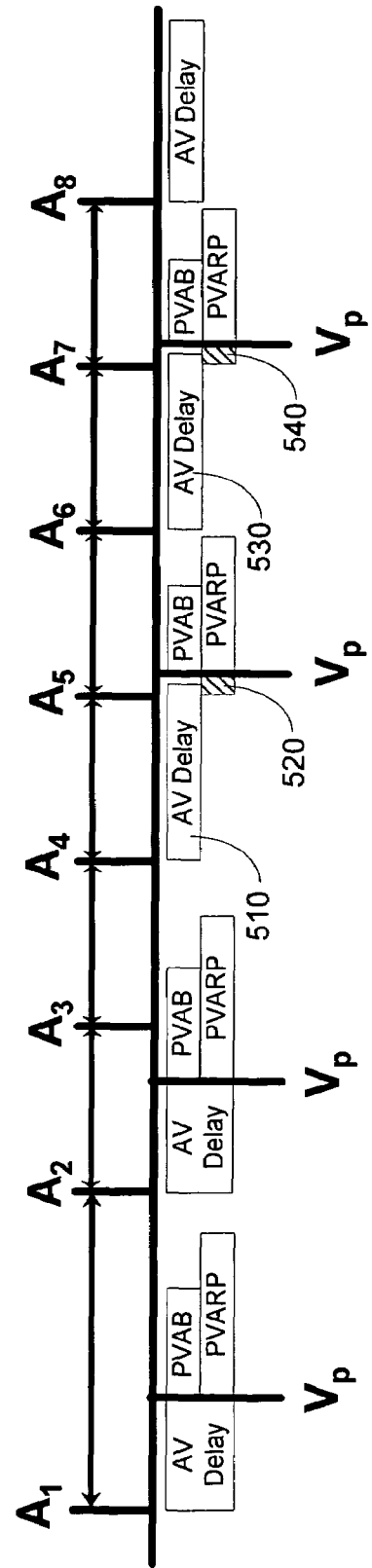

FIGS. 5A and 5B are timing diagrams illustrating synchronized ventricular pacing in accordance with embodiments of the invention. In this example, synchronized ventricular pacing is implemented when the atrial rate produces 2:1 ventricular pacing with undersensed atrial events, although the synchronized ventricular pacing may be implemented at any atrial rate.

FIG. 5A illustrates an atrial rate pattern that results in 2:1 ventricular pacing with undersensing of atrial events. Atrial events A1 and A2 each initiate an AV delay and the ventricle is paced, Vp, after expiration of the AV delay. However, starting with third atrial event, A3, every other atrial event (A3, A5, A7, etc.) is not sensed because the atrial event occurs during a post ventricular blanking period (PVAB).

FIG. 5B illustrates how synchronized ventricular pacing in accordance with embodiments of the invention may be implemented to reduce undersensing of atrial events. As in FIG. 5A, atrial events A1 and A2 each initiate an AV delay and the ventricle is paced, Vp, after expiration of the AV delay. Atrial event A3 is not sensed because it falls in a PVAB. At atrial event A4, the atrial rate has increased beyond the maximum tracking rate. Because the atrial rate exceeds the MTR, the AV delay 510 initiated by A4 is increased to a predetermined interval, such as the previous AV delay+about 10 ms, or to an interval used for detection of atrial tachyarrhythmia. Atrial event A5 is sensed during the extended AV delay 510 and initiates a second AV delay 520. The ventricle is paced following the second AV delay 520. The pacing cycle beginning with atrial event A6 is similar to the one that begins with A4. Because the atrial rate exceeds the MTR, the AV delay 530 initiated by A6 is extended. The atrial event A7 is sensed during the extended AV delay 530 and is used to initiate a second AV delay 540. The ventricle is paced following the second AV delay 540. Thus, the ventricular pacing synchronized to A5 places the atrial refractory period between atrial events A5 and A6 and the ventricular pacing synchronized to A7 places the atrial refractory period between atrial events A7 and A8. Placing the atrial refractory period between atrial events reduces undersensing of atrial events and enhances detection of atrial tachyarrhythmia as described above.

FIG. 5B illustrates one implementation of synchronized ventricular pacing in accordance with embodiments of the invention. In this example, the synchronized ventricular pacing is triggered when the AV delay is extended because the atrial rate that exceeds the MTR. In another implementation, the synchronized ventricular pacing of the present invention may be triggered by detection of a premature atrial contraction. In yet another embodiment, the synchronized ventricular pacing may be triggered based on a pattern of atrial intervals, such as a short-long pattern, where the long atrial intervals are about twice the length of the short atrial intervals.

In yet another implementation, synchronized ventricular pacing in accordance with embodiments of the invention may be triggered during a pacing response to detection of atrial flutter (AFL). Some CRM devices are capable of responding to detected atrial flutter to reduce the likelihood of pacing into the atrial vulnerable period and/or to provide a decrease in the ventricular pacing rate for atrial rates higher than a programmable atrial flutter response rate. In one implementation of atrial flutter response, a detected atrial event within PVARP or within a previously initiated AFR interval (AFRI) will start an AFR interval of a predetermined duration, e.g., about 260 ms. Detection of atrial events inside the AFRI will be classified as refractory events and will not be tracked. Tracking begins again after both the AFRI and the PVARP have expired. Paced atrial events scheduled to occur inside an AFRI may be delayed until the AFRI has expired or may be canceled.

Synchronized ventricular pacing in accordance with embodiments of the invention may be used in conjunction with atrial flutter response such as the implementation described immediately above. In accordance with an embodiment of the invention, when more than one AFRI is triggered since the previous ventricular pace and if an atrial event is detected within a predetermined time interval, which may be calculated using a previous ventricular interval, for example, then the atrial event is used to initiate an AV delay and the ventricle is paced following the AV delay. The time interval based on the previous ventricular interval may comprise an immediately previous ventricular interval or an average of several previous intervals, for example. The time interval may comprise a fraction (e.g., about ½, or other fraction) of an interval used for atrial tachyarrhythmia detection, or the AV delay interval, or the interval used for atrial tachyarrhythmia detection subtracted from the lower rate limit interval, for example.

Figure 6:
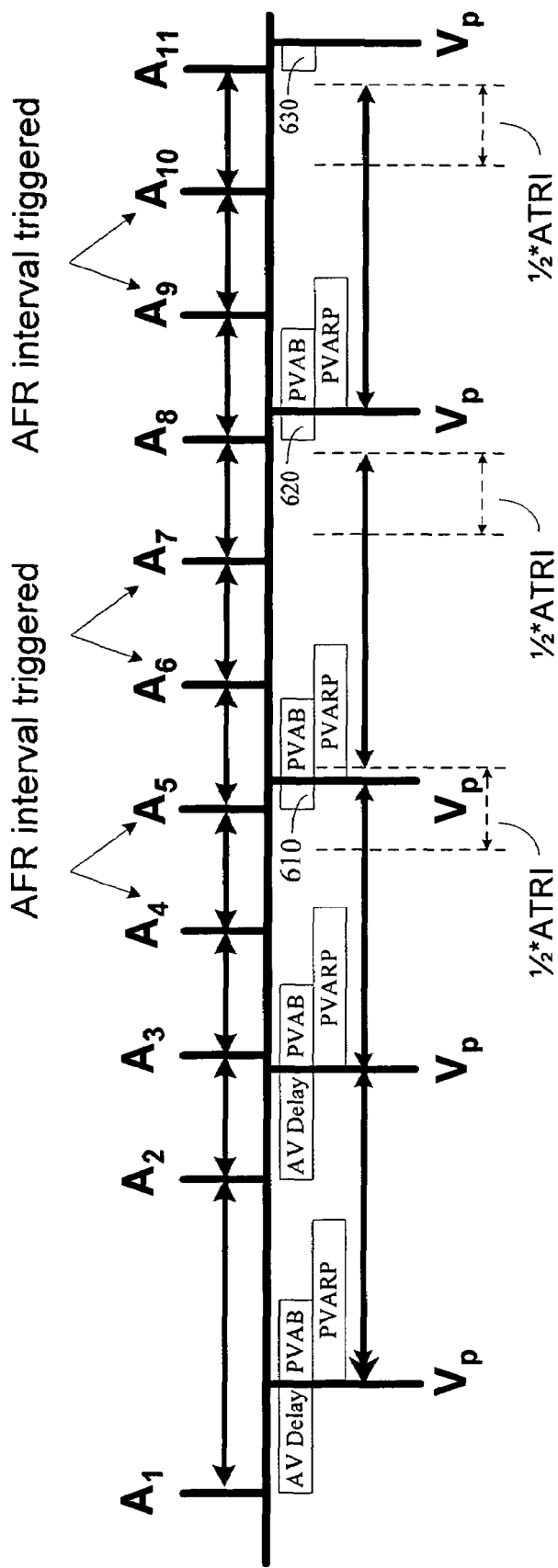
FIG. 6 is a timing diagram illustrating synchronized ventricular pacing during atrial flutter response in accordance with embodiments of the invention.

FIG. 6 is a timing diagram illustrating the use of synchronized ventricular pacing with atrial flutter response in accordance with embodiments of the invention. Atrial events A1 and A2 are sensed events and each of A1 and A2 initiate an AV delay with a ventricular pace, Vp, delivered following the AV delay. Atrial event A3 occurs during the PVAB and is not sensed. Atrial event A4 occurs during the post ventricular atrial refractory period initiated by the ventricular pace following A2. Atrial event A4 is a refractory event, therefore atrial event A4 triggers an AFR interval. Because the AFR interval has not expired prior to A5, A5 triggers a second AFR interval. Further, atrial event A5 occurs after a predetermined delay interval calculated from the immediately previous V event and based on a current pacing interval. In this example, the predetermined time interval comprises the current pacing interval minus ½ ATRI, wherein ATRI is the interval used for detecting atrial tachyarrhythmia. A short AV delay 610 is initiated by A5 and the ventricle is paced following the AV delay 610.

Atrial event A6 occurs during the post ventricular atrial refractory period initiated by the ventricular pace following A5. Atrial event A6 is thus a refractory event, and triggers an AFR interval. Because the AFR interval initiated by A6 has not expired prior to A7, A7 triggers a second AFR interval. A7 occurs before a predetermined delay interval calculated from the immediately previous V event and based on a current pacing interval. In this example, the predetermined delay interval comprises the current pacing interval minus ½ ATRI. Pacing is not delivered after A7. A8 occurs after the current pacing interval. A short AV delay 620 is initiated by A8 and the ventricle is paced following the AV delay 620. The atrial events A9 and A10 also trigger AFR intervals and pacing occurs as described above with a short AV delay 630 initiated by atrial event A11. When rate smoothing is on, the pacing rate gradually decreases. When the A-A intervals are regular and an integer multiple of A-A intervals fits between the current pacing rate and the maximum pacing rate, the atrial sensing capability is preserved.

Figure 7:
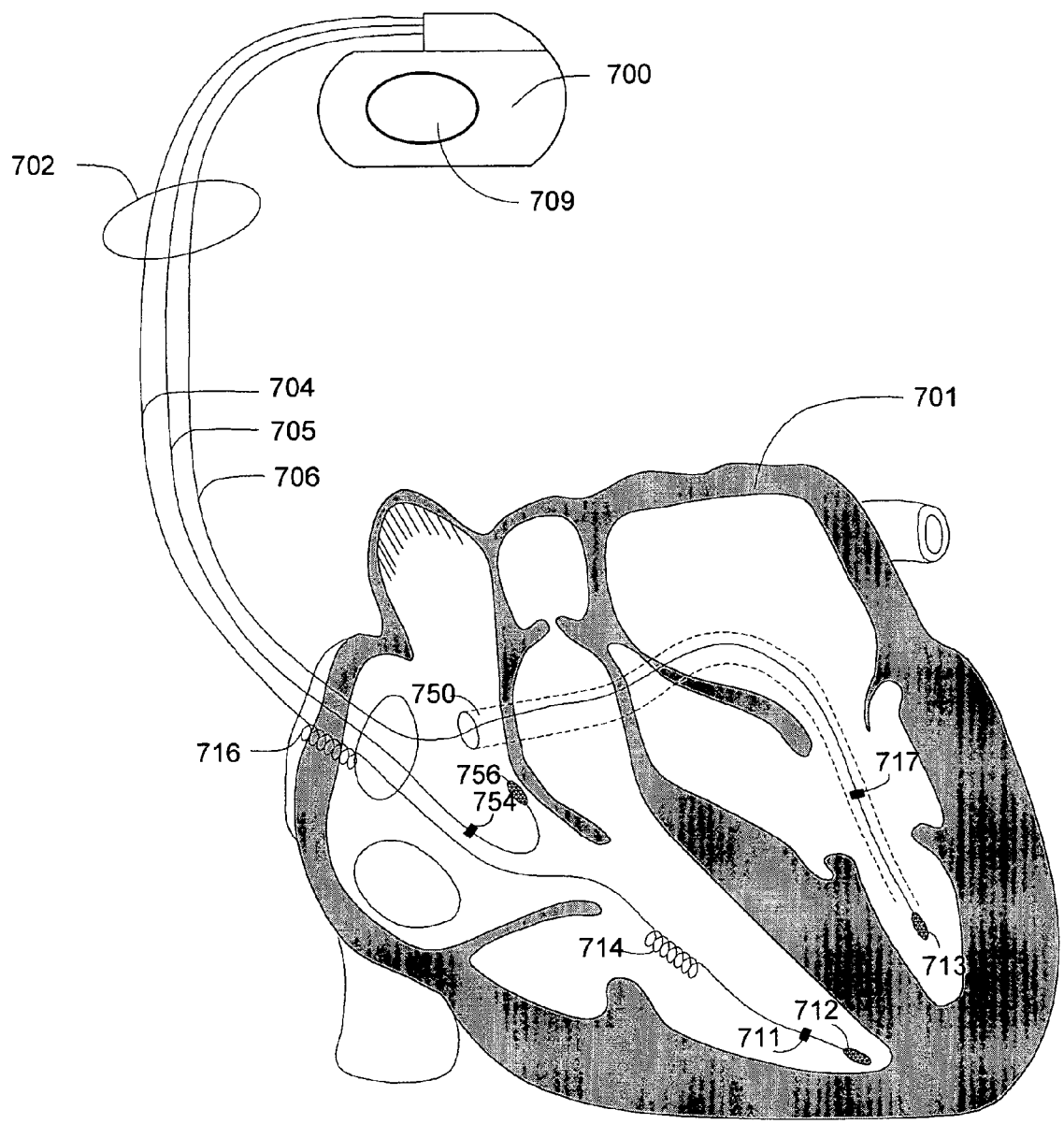
FIG. 7 is a partial view of a cardiac rhythm management (CRM) device that may be used to implement synchronized ventricular pacing to promote atrial sensing in accordance with embodiments of the invention.

FIG. 7 is a partial view of a cardiac rhythm management (CRM) device that may be used to implement synchronized ventricular pacing in accordance with embodiments of the invention. Methods of the invention may be implemented in a variety of implantable or patient-external cardiac therapeutic and/or diagnostic devices including, for example, pacemakers, defibrillators, cardioverters, bi-ventricular pacemakers, and/or cardiac resynchronization devices, among others. The CRM device illustrated in FIG. 7 includes an implantable housing 700 containing circuitry electrically coupled to an intracardiac lead system 702. Portions of the implantable housing may be configured as a can electrode 709. The housing 700 and the intracardiac lead system 702 is implanted in a human body with portions of the intracardiac lead system 702 inserted into a heart 701. The intracardiac lead system 702 is used to detect electric cardiac signals produced by the heart 701 and to provide electrical energy to the heart 701 under predetermined conditions to treat cardiac arrhythmias.

The intracardiac lead system 702 includes one or more electrodes used for pacing, sensing, and/or defibrillation. In the particular embodiment shown in FIG. 7, the intracardiac lead system 702 includes a right ventricular lead system 704, a right atrial lead system 705, and a left ventricular lead system 706. In one embodiment, the right ventricular lead system 704 is configured as an integrated bipolar pace/shock lead.

The right ventricular lead system 704 includes an SVC-coil 716, an RV-coil 714, and an RV-tip electrode 712. The RV-coil 714, which may alternatively be configured as a separate defibrillation coil and an RV-ring electrode 711, is spaced apart from the RV-tip electrode 712, which is a pacing electrode for the right ventricle.

The right atrial lead system 705 includes a RA-tip electrode 756 and an RA-ring electrode 754. The RA-tip 756 and RA-ring 754 electrodes may provide pacing pulses to the right atrium of the heart and may also be used to detect cardiac signals from the right atrium. In one configuration, the right atrial lead system 705 is configured as a J-lead.

In the configuration of FIG. 7, portions of the intracardiac lead system 702 are shown positioned within the heart 701, with the right ventricular lead system 704 extending through the right atrium and into the right ventricle. Typical locations for placement of the RV-tip electrode 712 are at the right ventricular (RV) apex or the RV outflow tract.

In particular, the RV-tip electrode 712 and RV-coil electrode 714 are positioned at appropriate locations within the right ventricle. The SVC-coil 716 is positioned at an appropriate location within a major vein leading to the right atrium chamber of the heart 701. The RV-coil 714 and SVC-coil 716 depicted in FIG. 7 are defibrillation electrodes.

The left ventricular lead system 706 is advanced through the superior vena cava (SVC), the right atrium 720, the ostium of the coronary sinus, and the coronary sinus 750. The left ventricular lead system 706 is guided through the coronary sinus 750 to a coronary vein of the left ventricle 724. This vein is used as an access pathway for leads to reach the surfaces of the left atrium and the left ventricle which are not directly accessible from the right side of the heart. Lead placement for the left ventricular lead system may be achieved via subclavian vein access and a preformed guiding catheter for insertion of the left ventricular (LV) electrodes 713 and 717 adjacent the left ventricle. In one configuration, the left ventricular lead system 206 is implemented as a single-pass lead.

An LV distal electrode 713, and an LV proximal electrode 717 may be positioned adjacent to the left ventricle. The LV proximal electrode 717 is spaced apart from the LV distal electrode, 713 which is a pacing electrode for the left ventricle. The LV distal 713 and LV proximal 717 electrodes may also be used for sensing the left ventricle.

The lead configurations illustrated in FIG. 7 represent one illustrative example. Additional lead/electrode configurations may include additional and/or alternative intracardiac electrodes and/or epicardial electrodes. For example, in one configuration, an extracardiac lead may be used to position epicardial electrodes adjacent the left atrium for delivering electrical stimulation to the left atrium and/or sensing electrical activity of the left atrium.

Figure 8:
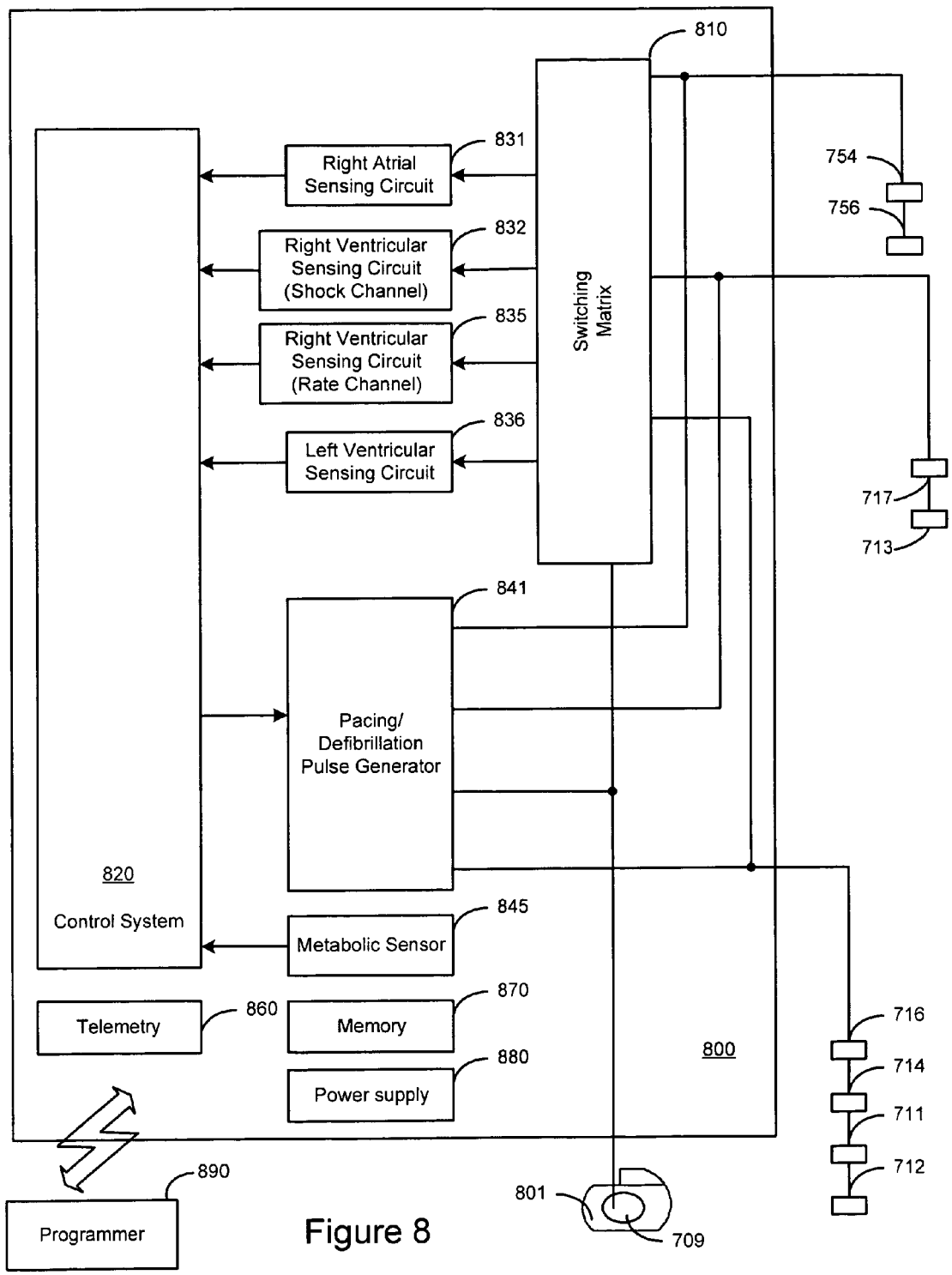
FIG. 8 is a block diagram of a cardiac rhythm management (CRM) device suitable for implementing synchronized ventricular pacing to promote atrial sensing in accordance with embodiments of the invention.

Referring now to FIG. 8, there is shown a block diagram of a cardiac rhythm management (CRM) device 800 suitable for implementing synchronized ventricular pacing in accordance with embodiments of the invention. FIG. 8 shows a CRM device 800 divided into functional blocks. It is understood by those skilled in the art that there exist many possible configurations in which these functional blocks can be arranged. The example depicted in FIG. 8 is one possible functional arrangement. Various functions of the CRM device 800 may be accomplished by hardware, software, or a combination of hardware and software.

The CRM device 800 includes components for sensing cardiac signals from a heart and delivering therapy, e.g., pacing pulses or cardioversion/defibrillation shocks, to the heart. The circuitry of the CRM device 800 may be encased and hermetically sealed in a housing 801 suitable for implanting in a human body. Power to the circuitry is supplied by an electrochemical battery power supply 880 that is enclosed within the housing 801. A connector block with lead terminals (not shown) is additionally attached to housing 801 to allow for the physical and electrical attachment of the intracardiac lead system conductors to the encased circuitry of the CRM device 800.

In one embodiment, the CRM device 800 comprises programmable microprocessor-based circuitry, including control circuitry 820, a memory circuit 870, sensing circuitry 831, 832, 835, 836, and a pulse generator 841. Components of the CRM device 800 cooperatively perform operations involving synchronized ventricular pacing according to the approaches of the present invention. The control circuitry 820 is responsible for arrhythmia detection, classification, and therapy control, including controlling synchronized ventricular pacing as described herein.

The memory circuit 870 may store program instructions used to implement the functions of the CRM device 800 as well as data acquired by the CRM device 800. For example, the memory circuit 870 may store historical records of sensed cardiac signals, including arrhythmic episodes, and/or information about therapy delivered to the patient. The memory circuit 870 may also store morphology templates representative of cardiac beats associated with various types of cardiac rhythms.

The historical data stored in the memory 870 may be used for various purposes, including diagnosis of patient diseases or disorders. Analysis of the historical data may be used to adjust the operations of the CRM device 800. Data stored in the memory 870 may be transmitted to an external programmer unit 890 or other computing device, such as an advanced patient management system as needed or desired.

Telemetry circuitry 860 allows the CRM device 800 to communicate with an external programmer unit 890 and/or other remote devices. In one embodiment, the telemetry circuitry 860 and the external programmer unit 890 use a wire loop antenna and a radio frequency telemetric link to receive and transmit signals. In this manner, programming commands and data may be transferred between the CRM device 800 and the external programmer 890 after implant.

The CRM device 800 may function as a pacemaker and/or a defibrillator. As a pacemaker, the CRM device 800 delivers a series of electrical stimulations to the heart to regulate heart rhythm. Therapy control circuitry 822 controls the delivery of pacing pulses to treat various arrhythmic conditions of the heart, for example. In various embodiments, the CRM device 800 may deliver pacing pulses to one or more of the right atrium, left atrium, right ventricle and the left ventricle. The heart may be paced to treat bradycardia, or to synchronize and/or coordinate contractions of the right and left ventricles. Pacing may be implemented in accordance with the processes of synchronized ventricular pacing as described above.

For example, right ventricular pacing may be implemented using unipolar or bipolar configurations. Unipolar RV pacing involves, for example, pacing pulses delivered between the RV-tip 712 to can 709 electrodes. Bipolar pacing involves, for example, delivery of pacing pulses between the RV-tip 712 to RV-coil 714 electrodes. If an RV-ring electrode is present, bipolar pacing may be accomplished by delivering the pacing pulses to the RV-tip 712 and RV-ring 711 electrodes.

Left ventricular pacing may be implemented using unipolar or bipolar configurations. Unipolar LV pacing may include, for example, pacing pulses delivered between the LV distal electrode 713 and the can 709. Alternatively, bipolar LV pacing may be accomplished by delivering the pacing pulses using the LV distal electrode 713 and the LV proximal electrode 717.

Similarly, unipolar (RA-tip electrode 756 to can electrode 709) atrial pacing or bipolar (RA-tip electrode 756 to RA-ring electrode 754) atrial pacing may be provided by the CRM device 800.

The CRM device 800 may also provide tachyarrhythmia therapy. For example, tachyarrhythmia therapy may be provided in the form of anti-tachycardia pacing (ATP) pulses delivered to an atrium or a ventricle. The ATP pulses may involve a series of timed paces of programmable width and amplitude that are implemented to interrupt a tachyarrhythmia episode. The ATP therapy may involve, for example, burst pacing at about 25 Hz to about 50 Hz. In various implementations, the pace-to-pace interval may have a variable or constant length. ATP therapy may be delivered to treat atrial flutter, for example. Therapy for atrial fibrillation may involve cardioversion shocks to the heart that may be initiated automatically or by the patient. Life threatening arrhythmias, such as ventricular fibrillation may be treated by one or more defibrillation shocks to the heart to terminate the fibrillation.

In the embodiment depicted in FIG. 8, electrodes RA-tip 756, RA-ring 754, RV-tip 712, RV-ring 711, RV-coil 714, SVC coil 716, LV distal electrode 713, LV proximal electrode 717, and can 709 are coupled through a switching matrix 810 to various sensing circuits 831, 832, 835, 836. A right atrial sensing channel circuit 831 serves to sense and amplify electrical signals from the right atrium of the heart. For example, bipolar sensing in the right atrium may be implemented by sensing signals developed between the RA-tip 756 and RA-ring 754 electrodes. The switch matrix 810 may be operated to couple the RA-tip 756 and RA-ring 754 electrodes to the RA sensing channel circuit 831 to effect bipolar sensing of right atrial signals. Alternatively, unipolar right atrial sensing may be accomplished by operating the switch matrix 810 to couple the RA-tip 756 and can 709 electrodes to the RA sensing channel circuit 831.

Cardiac signals sensed through the use of the RV-tip electrode 712 and RV-coil 714 or RV-ring electrode 711 are right ventricular (RV) near-field signals and are referred to as RV rate channel signals herein. Bipolar rate channel sensing may be accomplished by operating the switch matrix 810 to couple the RV-tip electrode 712 and the RV-coil 714 electrode or the RV-ring electrode 711 through the RV rate channel sensing circuitry 835. The rate channel signal may be detected, for example, as a voltage developed between the RV-tip electrode 712 and the RV-coil 714 electrode or the RV-ring electrode 711. The RV rate channel sensing circuitry 835 serves to sense and amplify the RV rate channel signal.

Unipolar RV sensing may be implemented, for example, by coupling the RV-tip 712 and can 709 electrodes to the RV rate channel sensing circuitry 835. In this configuration, the rate channel signal is detected as a voltage developed between the RV-tip 712 to can 709 sensing vector.

The RV lead system may also include an RV-ring electrode 711 used for bipolar pacing and sensing. If an RV-ring electrode is included in the lead system, bipolar sensing may be accomplished by sensing a voltage developed between the RV-tip 712 and RV-ring 711 electrodes.

Far-field signals, such as cardiac signals sensed through use of one of the defibrillation coils or electrodes 714, 716 and the can 709, or using both of the defibrillation coils or electrodes 714, 716, are referred to as morphology or shock channel signals herein. The shock channel signal may be detected as a voltage developed between the RV-coil 714 to the can electrode 709, the RV-coil 714 to the SVC-coil 716, or the RV-coil 714 to the can electrode 709 shorted to the SVC-coil 716. The switch matrix 810 is operated to couple the desired shock channel sensing vector, e.g., RV-coil to can, to the right ventricular shock channel sensing circuitry 832. The RV shock channel sensing circuitry 832 serves to sense and amplify the shock channel signal.

The outputs of the switching matrix 810 may also be operated to couple selected combinations of the electrodes to LV sensing channel circuitry 836 for sensing electrical activity of the left ventricle. Bipolar left ventricular sensing may be accomplished by operating the switch matrix 810 to couple the LV-distal 713 and the LV proximal electrodes 717 through the LV channel sensing circuitry 836. In this configuration, the LV signal is detected as a voltage developed between the LV proximal and LV distal electrodes.

Unipolar LV sensing may be implemented, for example, by coupling the LV distal 713 and can 709 electrodes to the LV sensing circuitry 736. In this configuration, the LV signal is detected as a voltage developed between the RV-tip 712 to can 709 sensing vector.

The CRM device 800 may incorporate one or more metabolic sensors 845 for sensing the activity and/or hemodynamic need of the patient. Rate-adaptive pacemakers typically utilize metabolic sensors to adapt the pacing rate to match the patient's hemodynamic need. A rate-adaptive pacing system may use an activity or respiration sensor to determine an appropriate pacing rate. Patient activity may be sensed, for example, using an accelerometer disposed within the housing of the pulse generator. Transthoracic impedance, which may be measured, for example, via the intracardiac electrodes, may be used to determine respiration rate. Sensor information from the metabolic sensor is used to adjust the pacing rate to support the patient's hemodynamic need. If the sensors indicate the patient's activity and/or respiration rate is high, then the patient's pacing rate is increased to correspond to the level of activity or rate of respiration.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of cardiac pacing, comprising:
   providing a first atrioventricular (AV) delay used for pacing a ventricle;
   modifying the first atrioventricular (AV) delay based on characteristics of previously sensed atrial events;
   using a first atrial event to initiate the modified AV delay;
   using a second atrial event to initiate, during the modified AV delay, a second AV delay if the second atrial event is sensed during the modified AV delay, the second AV delay being different than the modified AV delay; and
   delivering a ventricular pacing pulse at an end the second AV delay.

2. The method of claim 1, wherein modifying the first AV delay comprises extending the first AV delay if the atrial rate exceeds a maximum tracking rate.

3. The method of claim 1, wherein modifying the first atrioventricular (AV) delay based on the previously sensed atrial events comprises modifying the first atrioventricular delay based on detection of premature atrial contraction.

4. The method of claim 1, wherein modifying the first atrioventricular (AV) delay based on previously sensed atrial events comprises modifying the first atrioventricular delay based on detection of a short-long pattern of atrial events.

5. The method of claim 1, wherein the first atrial event comprises a non-refractory atrial event.

6. The method of claim 1, wherein a duration of the second AV delay is selected to enhance sensing of subsequent atrial events.

7. The method of claim 1, wherein a duration of the second AV delay is based on a post ventricular atrial blanking (PVAB) interval.

8. The method of claim 1, further comprising delivering the ventricular pacing pulse after a predetermined interval if the second atrial event is not sensed during the extended AV delay.

9. A cardiac pacing device, comprising:
   sensing circuitry configured to sense electrical signals of an atrium;
   a pulse generator configured to deliver electrical stimulation to a ventricle; and
   a processor configured to provide a first atrioventricular delay used for pacing and to modify the first atrioventricular delay based on characteristics of one or more previous atrial events and to implement the modified AV delay, the processor further configured to use a second atrial to initiate, during the modified AV delay, a second AV delay if the second atrial event is sensed during the modified AV delay and to control delivery of a ventricular pacing pulse at an end of the second AV delay the second AV delay being different than the modified AV delay.

10. The device of claim 9, wherein the processor is configured to modify the first atrioventricular delay based on a rate of the one or more previous atrial events.

11. The device of claim 9, wherein the processor is configured to modify the first atrioventricular delay based on a pattern of the one or more previous atrial events.

12. The device of claim 9, wherein the processor is configured to modify the first atrioventricular delay based on detection of a premature atrial contraction.

13. The device of claim 9, wherein the processor is further configured to detect atrial flutter and to initiate a pacing response based on the detection of atrial flutter.

14. The device of claim 13, wherein the pacing response comprises initiating one or more timing intervals based on detection of an atrial event sensed during a post ventricular atrial refractory period.

15. The device of claim 14, wherein the processor is configured to implement a second atrioventricular delay during at least one of the timing intervals and to control delivery of a ventricular pacing pulse relative to the second atrioventricular interval.

16. A cardiac pacing system, comprising:
 means for implementing a first atrioventricular (AV) delay relative to a non-refractory atrial event;
 means for modifying the first atrioventricular (AV) delay based on characteristics of previously sensed atrial events;
 means for initiating, during the modified AV delay, a second AV delay using a second atrial event if the second atrial event is sensed during the modified AV delay, the second AV delay being different than the modified AV delay; and
 means for delivering a ventricular pacing pulse at an end of the second AV delay.

17. The cardiac pacing system of claim 16, further comprising means for delivering the ventricular pacing pulse after the modified AV delay if the second atrial event is not sensed during the extended AV delay.

* * * * *

UNITED STATES PATENT AND TRADEMARK OFFICE
CERTIFICATE OF CORRECTION

PATENT NO. : 7,599,738 B2  Page 1 of 1
APPLICATION NO. : 11/130671
DATED : October 6, 2009
INVENTOR(S) : Jaeho Kim et al.

It is certified that error appears in the above-identified patent and that said Letters Patent is hereby corrected as shown below:

Column 12, Claim 1, line 23: "an end the" should be --an end of the--.

Column 12, Claim 8, line 45: "after a predetermined interval if" should be --after the modified AV delay if--.

Column 12, Claim 8, line 46: "the extended AV" should be --the modified AV--.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,599,738 B2  
APPLICATION NO. : 11/130671  
DATED : October 6, 2009  
INVENTOR(S) : Kim et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 609 days.

Signed and Sealed this

Twenty-eighth Day of September, 2010

David J. Kappos  
*Director of the United States Patent and Trademark Office*